United States Patent [19]

Stroppolo et al.

[11] Patent Number: 5,312,627
[45] Date of Patent: May 17, 1994

[54] TRANSDERMAL THERAPEUTIC SYSTEM FOR THE ADMINISTRATION OF DRUGS HAVING BRONCHODILATING ACTIVITY

[75] Inventors: Federico Stroppolo, Pregassona, Switzerland; Daniele Bonadeo, Varese; Annibale Gazzaniga, Rescaldina, both of Italy

[73] Assignee: Zambon Group S.p.A., Vicenza, Italy

[21] Appl. No.: 912,510

[22] Filed: Jul. 13, 1992

[30] Foreign Application Priority Data

Jul. 15, 1991 [IT] Italy .............. MI91A001950

[51] Int. Cl.$^5$ ............................... A61K 9/70
[52] U.S. Cl. ........................... 424/448; 424/443; 424/447; 424/449; 424/486; 604/305; 514/788.1
[58] Field of Search ............. 424/449, 448, 447, 443

[56] References Cited

U.S. PATENT DOCUMENTS

| | | | |
|---|---|---|---|
| 4,031,894 | 6/1977 | Urquhart et al. | 424/449 |
| 4,201,211 | 5/1980 | Chandrasekaran et al. | 424/449 |
| 4,292,302 | 9/1981 | Keith et al. | 424/449 |
| 4,699,777 | 10/1987 | Zupon et al. | 424/449 |
| 4,776,850 | 10/1988 | Guse et al. | 424/448 |
| 5,079,008 | 1/1992 | Sinnreich et al. | 424/448 |

FOREIGN PATENT DOCUMENTS

| | | |
|---|---|---|
| 0341202 | 11/1989 | European Pat. Off. |
| 0374980 | 6/1990 | European Pat. Off. |
| 2140019 | 11/1984 | United Kingdom |
| 9116085 | 10/1991 | World Int. Prop. O. |

OTHER PUBLICATIONS

USAN and the USP Dictionary of Drug Names, 1961–1990 Cumulative List (USAN 1991), p. 92.
The Merck Index, 11th Ed. (1989), pp. 37, 38, 278, 366, 376, 821, 889, 933, 1189–1190, 1376, 1442–1443, 1543.
S.T.P. Pharma Sciences 1 (1) pp. 5–23 (1991), Y. W. Chien "Transdermal Systemic Drug Delivery-Recent Development and . . . ".
Drug Development and Industrial Pharmacy, 16(9), pp. 1565–1577 (1990), Jain et al, "Salbutamol Delivering Transdermal . . . ".

*Primary Examiner*—Thurman K. Page
*Assistant Examiner*—Neil Levy
*Attorney, Agent, or Firm*—Stevens, Davis, Miller & Mosher

[57] ABSTRACT

A transdermal therapeutic system in polymer matrix for the administration of bronchodilator drugs is described, in which the matrix comprises a mixture of medium and high molecular weight polyisobutylene in a ratio comprised between 1 and 2.3.

7 Claims, No Drawings

TRANSDERMAL THERAPEUTIC SYSTEM FOR THE ADMINISTRATION OF DRUGS HAVING BRONCHODILATING ACTIVITY

The present invention relates to a transdermal therapeutic system for the administration of drugs having bronchodilating activity and more particularly relates to a transdermal therapeutic system in polymer matrix based on polyisobutylene suitable for the administration of said drugs.

The transdermal therapeutic systems (hereinafter indicated as TTSs-Transdermal Therapeutic Systems) in polymer matrix are one of the four different kinds of transdermal systems substantially existing in pharmaceutic technology (Y.W. Chien-"Transdermal Systemic Drug Delivery-Recent Development and Future Prospects"-S.T.P. Pharma Sciences, 1(1), 5-23, 1991).

Said systems in polymer matrix are characterized by the presence of the drug homogeneously distributed in solid form in a polymer matrix having defined surface and thickness. From this matrix the drug is released directly by mere diffusion.

TTSs in polymer matrix are structurally simpler than the other TTSs that are generally classified as systems with a controlling membrane or "reservoir" systems in which the release rate is regulated by a suitable membrane, systems with a gradient concentration in which the profile of the drug release is obtained by setting up a multilayer of laminates containing increasing doses of drug and systems with microreservoir in which a suspension of the drug in form of microscopic particles is dispersed by means of particular techniques, in a hydrophobic polymer.

The development of a TTS requires an accurate study of the utilized materials. This is particularly important for the TTS in polymer matrix in which the interaction between drug and polymer is complete since the drug not only goes across the polymer but also results to be physically dispersed therein.

Therefore, it clearly appears that the formulation of a TTS in polymer matrix gives rise to some problems that cannot be easily solved. In fact the formulation of a polymer with other components, mainly the drug itself, can influence its physico-chemical characteristics, thus creating incompatibility problems.

Moreover the polymeric material should show diffusional characteristics suitable to ensure, for a determined class of drugs, the achievement of a delivery rate useful for the therapeutic treatment. At the same time, it must not be incompatible with the other components of the formulation, namely, it must maintain physical characteristics suitable for the preparation of the TTSs.

Polyisobutylene is an adhesive polymer available on the market in different forms, which differ among each other for the different molecular weights.

For simplicity hereinafter we shall indicate the polyisobutylenes in the following way on the base of their molecular weights (expressed as "Viscosity Average Relative Molecular Mass"):
  low molecular weight polyisobutylene: having molecular weight from 500 up to 5,000
  medium molecular weight polyisobutylene: having molecular weight higher than 5,000 up to 500,000
  high molecular weight polyisobutylene: having molecular weight higher than 500,000.

The use of polyisobutylene in the formulation of TTSs is known. U.S. Pat. No. 4,031,894 (Alza Corporation) describes a TTS with a controlling membrane containing scopolamine as active ingredient. In this system, which is commercialized with the registered trademark "Transderm-Scop", the drug is dispersed in a "reservoir" layer consisting of a mixture of mineral oil (35-65% by weight) and polyisobutylene (35-65% by weight). The polymeric portion in turn consist of a mixture of medium molecular weight polyisobutylene (10-40% by weight) and high molecular weight polyisobutylene (20-40% by weight). From this "reservoir" layer the scopolamine release is regulated by a microporous controlling membrane.

To the controlling membrane a further layer, consisting of a mixture of mineral oil and polyisobutylene in the same ratios as above, is affixed. When the TTS must be used this last layer, which is in direct contact with the skin, immediately releases the drug therein contained.

U.S. Pat. No. 4,201,211 (Alza Corporation) describes a TTS completely analogous to the previous one with a controlling membrane for the administration of clonidine.

British patent application No. 2,140,019 (Alza Corporation) describes an improvement of the TTSs of U.S. Pat. Nos. 4,031,894 and 4,201,211 by the addition of colloidal silicon dioxide to the mixture of mineral oil and polyisobutylene. This addition improves the mechanical and diffusional properties of the TTS and makes it suitable for the administration of drugs moderately soluble in mineral oil. A TTS of this kind, containing clonidine, is commercialized with the registered trademark "Catapres-TTS".

The transdermal systems based on mixtures of mineral oil and polyisobutylene known up to now have however the drawback of releasing very quickly the drug and of requiring therefore the presence of a controlling membrane that regulates the release rate, in order to get a slow and prolonged release.

The need of administrating bronchodilator drugs in pharmaceutical forms allowing to maintain the plasmatic level of active ingredient within the therapeutic range, for a time as long as possible, is a long felt need in the medical field.

Many drugs having bronchodilating activity known from the literature can be useful in the treatment of bronchospasm and in particular of the bronchial asthma, by oral administration or inhalation. However, in the oral administration, these drugs, that are generally characterized by a low half-life, need frequent administrations and therefore they are not able to prevent nocturnal seizures that are frequent in asthmatic patients.

The transdermal administration of bronchodilators in TTSs, capable of assuring a prolonged and defined action, thanks to the maintenance of therapeutically effective and constant blood levels and the contemporaneous decrease of side-effects by means of optimization of the plasmatic concentration/time profiles, would constitute an optimal solution from the therapeutic point of view in the treatment of bronchial asthma.

Transdermal systems containing bronchodilators as active ingredient have been already described in the literature. For example an osmotic transdermal device with a controlling membrane has been studied for the administration of salbutamol [S. K. Jaim et al., Drug Development and Industrial Pharmacy, 16(9), 1565-1577, (1990)].

In U.S. Pat. No. 4,292,302 (Key Pharmaceutical Inc.) a TTS in polymer matrix is described, containing t.butaline, consisting of a polar plasticizer, polyvinylalcohol and polyvinylpyrrolidone. European patent application No. 374980 (Nitto Denko Corporation) describes a TTS in polymer matrix for the administration of tulobuterol, in which the matrix consists of high molecular weight polyisobutylene blended with low and medium molecular weight polyisobutylene and a thermoplastic resin.

The thermoplastic resin has the purpose of slowing down the diffusion and the migration of the active ingredient in the matrix, in order to achieve an effective transdermal release.

In fact without such resin the active ingredient release does not occur in a slow and prolonged way, but on the contrary, it is such as to achieve blood concentrations from 2.5 to 7 times higher than the values obtained by using the resin during the first 8 hours of administration, and such as to decrease below the effective value within 24 hours (see table 3 of the Nitto patent application).

International patent application No. WO 91/16085 (published on Oct. 31, 1991) describes a transdermal delivery device comprising a mixture of high and low molecular weight polyisobutylene (HMW and LMW respectively) having a weight ratio HMW PIB:LMW PIB in the range of about 5-40:95-60, which is substantially free from plasticizers and tackifiers, which comprises an oily, non-polar active agent dissolved in the polymeric component, optionally containing a drug reservoir.

However even such a kind of TTS would release too quickly the oily active agent, in fact, in all the Examples the devices prepared comprise also a drug reservoir and a rate-controlling membrane (made of a thermoplastic resin).

We have now found that bronchodilator drugs can be administered by transdermal route by employing a system in polymer matrix constituted by a mixture of high and medium molecular weight polyisobutylene thus obtaining a slow and prolonged release of the active ingredient particularly effective in the treatment of bronchial asthma.

Therefore, object of the present invention is a transdermal therapeutic system in polymer matrix for the administration of drugs having bronchodilating activity, in which the drug is suspended in solid form and in which the matrix comprises from 10% to 60% by weight of medium molecular weight polyisobutylene and from 9% to 25% by weight of high molecular weight polyisobutylene, the weight ratio between medium molecular weight and high molecular weight polyisobutylene being comprised between 1 and 2.3.

Preferably the medium molecular weight polyisobutylene employed in the present invention has a molecular weight comprised between 10,000 and 200,000, more preferably between 30,000 and 50,000, and the high molecular weight polyisobutylene has a molecular weight comprised between 500,000 and 1,500,000, more preferably between 1,000,000 and 1,300,000.

The polyisobutylene polymer matrix contains the drug in a dispersed form in amounts preferably comprised between 10% and 50% by weight and the matrix surface, which is directly in contact with the skin, acts as release surface through which the drug gradually spreads and is slowly absorbed for a prolonged period of time. Specific examples of bronchodilator drugs suitable for the TTS in polymer matrix of the present invention are compounds having an arylethanolaminic structure of formula

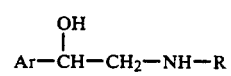

wherein Ar is a substituted aryl and R is an isopropyl or tert-butyl group and in particular:

Albuterol-Ar=4-hydroxy-3-hydroxymethyl-phenyl (salbutamol) R=tert-butyl (Merck Index, 11th ed., No. 209)

Broxaterol-Ar=3-bromo-isoxazol-5-yl R=tert-butyl (USAN and USP Dictionary of Drug Names, 1991)

Carbuterol-Ar=4-hydroxy-3-ureido-phenyl R=tert-butyl (Merck Index, 11th ed., No. 1840)

Clenbuterol-Ar=4-amino-3,5-dichloro-phenyl R=tert-butyl (Merck Index, 11th ed., No. 2347)

Clorprenaline-Ar=2-chloro-phenyl R=isopropyl (Merck Index, 11th ed., No. 2404)

Isoproterenol-Ar=3,4-dihydroxy-phenyl R=isopropyl (Merck Index, 11th ed., No. 5105)

Mabuterol-Ar=4-amino-3-chloro-5-trifluoromethyl-phenyl R=tert-butyl (Merck Index, 11th ed., No. 5517)

Metaproterenol-Ar=3,5-dihydroxy-phenyl R=isopropyl (Merck Index, 11th ed., No. 5836)

Pirbuterol-Ar=3-hydroxy-2-hydroxymethyl-piridin-2-yl R=tert-butyl (Merck Index, 11th ed., No. 7461)

Soterenol-Ar=4-hydroxy-3-methanesulphonylamino-phenyl R=isopropyl (Merck Index, 11th ed., No. 8683)

Terbutaline-Ar=3,5-dihydroxy-phenyl R=tert-butyl (Merck Index, 11th ed., No. 9089)

Tulobuterol-Ar=2-chloro-phenyl R=tert-butyl (Merck Index, 11th ed., No. 9720)

and their possible stereoisomeric forms or biological precursors. Preferred drugs are broxaterol and albuterol.

Preferred transdermal systems according to the invention are transdermal therapeutic systems containing from 20 to 40% by weight of broxaterol or albuterol as active ingredient.

Optionally the polymer matrix of the TTS of the present invention can contain a further excipient which has the purpose of optimizing the formulation characteristics of the final product.

Preferably hydrophilic excipients, selected among carbohydrates, such as for example, lactose, polyalcohols such as for example sorbitol, mannitol and solid polyethyleneglycols such as for example PEG 4000, in amounts from 4% to 20% by weight or lipophilic excipients selected among saturated hydrocarbons such as mineral oil and squalane in amounts from 20 to 40% are incorporated in the polymer matrix.

It is important to point out that the polymer matrix of the TTS of the invention is characterized by the sole presence of a mixture of medium and high molecular weight polyisobutylene in a weight ratio comprised between 1 and 2.3.

In other words the incorporation of a bronchodilating active ingredient in a matrix according to the invention allows to make a transdermal system in polymer matrix having release characteristics suitable in the therapeutic treatment, namely it allows to obtain a constant and prolonged permeation of the drug by mere diffusion from the matrix to the skin surface.

This peculiar aspect of the TTS in polymer matrix according to the invention is what mainly distinguishes it from the known technique. In fact, although the use of mixtures of different molecular weight polyisobutylene was known in the preparation of transdermal systems, such a use always led to the achievement of matrixes having a release rate which required a controlling membrane or the incorporation of suitable excipient in order to slow down the active ingredient flow.

On the contrary, as already pointed out, by using the TTSs of the invention a constant and prolonged permeation of the active ingredient through the skin is obtained. This is due to the diffusional properties of the matrix that are bound mainly to the presence of the polyisobutylenic mixture in the indicated weight ratios.

As it will be explained more in detail in the examples, the presence in the matrix of other components, among which the active ingredient itself should be considered, does not significantly modify the permeation profile, but allows to modulate and optimize the characteristics of the finished product such as adhesiveness and viscosity.

The selection of the appropriate combination of components, within the scope of values according to the invention, depends mainly upon the pharmacological characteristics of the specific active ingredient (optimal therapeutic dose and consequential permeation rate required) and in minor extent upon its physico-chemical characteristics.

However, the variation of the parameters, in order to get the sought permeation rate for each specific single active ingredient, falls within the scope of the ordinary knowledge of the man skilled in the art.

In general, for the formulation of the TTS according to the invention, the man skilled in the art must take into consideration the following observations.

An increase of the drug surface area helps the homogeneous dispersion in the matrix, the thickness of the matrix being the same. The incorporation of a hydrophilic excipient in the matrix produces a decrease of adhesiveness, while the incorporation of a lipophilic excipient leads to an increase of adhesiveness.

An increased amount of high molecular weight polyisobutylene reduces the adhesiveness of the matrix and puts up the viscosity. The preparation of the TTS according to the invention is carried out according to conventional techniques (deposition, drying, lamination and reduction to release unity).

A suspension of the mixture of medium and high molecular weight polyisobutylene, of the active ingredient and further possible components is first put on a suitable substrate, generally consisting of a film of polymeric material, that in the finished TTS will act as protecting coating to be removed when it must be used. By subsequent drying the medicated polymer matrix of the sought thickness is obtained, on which the protecting support, namely the most external layer of the transdermal system, is affixed by lamination.

Also the protecting support generally consists of a film of polymeric material such as polyethylene, polypropylene, polyvinylchloride and polyethylene terephthalate or thin laminates of aluminum or other suitable materials.

The laminate thus obtained, consisting of the substrate, the matrix and the protecting support, is then reduced to single mono-dose release units having the sought surface.

Alternatively, the deposition step can be carried out on the protecting support. Consequently the lamination step will be the addition on the matrix of the protecting coating to be removed when it must be used.

The matrix surface and thickness are not critical but they are appropriately selected depending on the active ingredient dose to be administered. However in general TTSs having a release surface from 0.5 to 4 $cm^2$ are preferred for this use.

The TTS in polymer matrix of the invention shows some advantages that are evident to the man skilled in the art.

From a technological point of view they represent the simplest and most easily feasible solution and consequently the cheapest solution.

The materials employed are already approved by various public health authorities for use in the pharmaceutical field.

Moreover, as already pointed out, the TTS of the invention allows to administrate bronchodilating drugs by mere diffusion from the matrix to the skin surface thus obtaining a constant and prolonged drug permeation.

From a therapeutic point of view, the characteristics of constant and prolonged permeation of the bronchodilating drugs by administration with the TTS of the invention allow to avoid the side-effects due to peaks of plasmatic concentration of the drugs, generally obtained by oral treatment. At the same time the frequency of administration is reduced, still allowing, for instance, an effective treatment of the nocturnal asthmatic seizures.

In order to better illustrate the present invention the following examples are now given.

EXAMPLE 1

Preparation of Transdermal Formulations Containing Broxaterol as Active Ingredient General method The materials employed for the preparation of the single mono-dose release units were the following:

Broxaterol having surface area 1.63 $m^2/g$

Oppanol ® B10: registered trademark of BASF for a polyisobutylene having molecular weight of 40,000

Oppanol ® B100: registered trademark of BASF for a polyisobutylene having molecular weight of 1,270,000

2009 Scotchpak Polyester Film Laminate, commercialized by 3M, as support.

1022 Scotchpak Fluoropolymer Coated Liner, commercialized by 3M, as protecting coating.

A solution of Oppanol ® B10 in n-hexane at a concentration of 50% by weight and a solution of Oppanol ® B100 in n-hexane at a concentration of 9% by weight are prepared.

The two solutions were mixed and to the mixture the other components in suspension were added, thus obtaining certain suspensions which were used for the preparation of the matrixes.

The qualitative and quantitative composition of said suspensions is reported in the following table.

TABLE 1

Qualitative and quantitative composition of the suspensions employed for the preparation of the matrixes. The values are expressed as g/100 g.

| Components | Suspension | | | | | | | | | |
|---|---|---|---|---|---|---|---|---|---|---|
| | I | II | III | IV | V | VI | VII | VIII | IX | X |
| Broxaterol | 5.02 | 8.32 | 12.40 | 8.40 | 8.70 | 9.30 | 10.50 | 11.20 | 14.10 | 9.64 |
| Oppanol B10 | 14.04 | 13.56 | 12.96 | 12.85 | 12.65 | 12.95 | 12.25 | 11.75 | 9.90 | 5.33 |
| Oppanol B100 | 6.02 | 5.81 | 5.55 | 5.83 | 5.70 | 5.55 | 5.22 | 5.04 | 4.25 | 5.33 |
| Lactose | — | — | — | 1.10 | 2.30 | — | — | — | — | — |
| PEG 4000 | — | — | — | — | — | 3.10 | 7.00 | — | — | — |
| Mineral oil | — | — | — | — | — | — | — | 9.30 | 18.90 | 14.20 |
| n-hexane | 74.91 | 72.31 | 69.09 | 71.82 | 70.65 | 69.10 | 65.03 | 62.71 | 52.85 | 65.50 |

The suspensions were then applied with a pre-established thickness (0.6–0.8 mm) on 1022 Scotchpak Fluoropolymer Coated Liner, they were dried first at 25° C. for 24 hours then at 50° C. for 45 minutes. On the matrixes thus obtained the support (2009 Scotchpack Polyester Film Laminate) was affixed by lamination and the laminate was then cut in units of 0.64 cm² by drinking.

The qualitative and quantitative composition of the medicated matrixes of the formulations thus obtained is reported in the following table.

TABLE 2

Qualitative and quantitative composition of the medicated matrixes. The values are expressed as g/100 g.

| Components | Suspension | | | | | | | | | |
|---|---|---|---|---|---|---|---|---|---|---|
| | I | II | III | IV | V | VI | VII | VIII | IX | X |
| Broxaterol | 20.0 | 30.0 | 40.0 | 30.0 | 30.0 | 30.0 | 30.0 | 30.0 | 30.0 | 30.0 |
| Oppanol B10 | 56.0 | 49.0 | 41.9 | 45.5 | 43.3 | 42.0 | 35.0 | 31.5 | 21.0 | 15.0 |
| Oppanol B100 | 24.0 | 21.0 | 18.1 | 19.5 | 18.6 | 18.0 | 15.0 | 13.5 | 9.0 | 15.0 |
| Lactose | — | — | — | 4.0 | 8.0 | — | — | — | — | — |
| PEG 4000 | — | — | — | — | — | 10.0 | 20.0 | — | — | — |
| Mineral oil | — | — | — | — | — | — | — | 25.0 | 40.0 | 40.0 |

EXAMPLE 2

Determination of transcutaneous permeation of transdermal formulations containing broxaterol as active ingredient The evaluation of the permeation of broxaterol released by the formulations I-X, prepared as described in example 1, was carried out on human skin by employing the Franz cell.

The transdermal formulations, fixed on an adhesive support, were to adhered, after having removed the protective coating, to the horny layer surface of the skin sample (about 3 cm²), which was previously located at the top of the receiving section of a Franz cell.

The receiving section contains a buffer solution (4.5 ml) prepared by mixing a 0.1M solution of $NaH_2PO_4$ $H_2O$ with a suitable amount of a 5M solution of NaOH up to pH 6.

The determination of broxaterol present in the receiving section was carried out by HPLC under the following conditions:

Equipment:
  pump (Jasco mod. 880-PU)
  detector (Jasco mod. 875-PU)
  valve (Rheodyne mod. 7010 on Autosample Gilson mod. 231)
  integrator (Spectra Physics SP 4270 Shimadzu Chromatopack CR-5A)
  column (Supelco LC-18DB, 5 µm 150×4.6 mm)
  pre-column (Supelco LC-18DB, 2 cm)
Chromatographic conditions:

Mobile phase: 0.01M solution of $KH_2PO_4$ acidified up to pH 2.9 with $H_3PO_4$. To this solution methanol was added (80:20) and then triethylamine (200 µl/l)
flow rate: 1.5 ml/minute
wave length: 217 nm
temperature: room temperature
injected volume: 20 µl
retention time: about 4.3 minutes.

The samples from the receiving section were carried out after 6.12 and 24 hours.

The tests were repeated on 6 samples for each formulation.

In the following table are reported the data of maximum and medium flow that are indexes of the permeation rate.

As maximum flow was considered the amount of permeated drug between the 12$^{th}$ and the 24$^{th}$ hour (from the beginning of the test) per time unit and surface unit of the matrix (µg/cm²/h).

As average flow was considered the amount of drug permeated between time 0 and the 24$^{th}$ hour (from the beginning of the test) per time unit and surface unit (µg/cm²/h).

TABLE 3

Values of maximum and medium flow of broxaterol (between brackets standard deviation), expressed as µg/cm²/h, permeated through the skin (formulations I-X).

| Formulation | Maximum flow µg/cm²/h (±S.D.) | Average flow µg/cm²/h (±S.D.) |
|---|---|---|
| I | 7.5 (±2.9) | 4.5 (±1.5) |
| II | 10.7 (±4.0) | 6.4 (±2.2) |
| III | 13.1 (±4.6) | 8.7 (±3.4) |
| IV | 10.2 (±1.6) | 6.4 (±0.6) |
| V | 12.8 (±4.3) | 8.8 (±2.5) |
| VI | 10.6 (±4.6) | 7.1 (±2.9) |
| VII | 18.7 (±6.8) | 12.6 (±4.7) |
| VIII | 14.5 (±5.6) | 10.0 (±3.5) |
| IX | 18.4 (±4.5) | 12.4 (±3.1) |
| X | 30.8 (±4.0) | 18.3 (±2.5) |

What we claim is:

1. A transdermal therapeutic system in polymer matrix for the administration of drugs having bronchodilating activity, said system consisting essentially of a substance having bronchodilating activity suspended in solid form and a matrix in which said substance is suspended, said matrix comprising from 10% to 60% by weight of medium molecular weight polyisobutylene having a molecular weight higher than 5,000 and up to 500,000 and from 9% to 25% by weight of high molecular weight polyisobutylene having a molecular weight higher than 500,000, the weight ratio between the medium and the high molecular weight polyisobutylene being from 1 to 2.3.

2. A transdermal therapeutic system according to claim 1 containing from 4% to 20% by weight of a hydrophilic excipient.

3. A transdermal therapeutic system according to claim 1 containing from 10% to 40% by weight of a lypophilic excipient.

4. A transdermal therapeutic system according to claim 1 in which the drug having bronchodilating activity is present in amounts from 10% to 50% by weight.

5. A transdermal therapeutic system according to claim 1 in which the active ingredient is selected among albuterol, broxaterol, carbuterol, clenbuterol, clorprenaline, isoproterenol, mabuterol, metaproterenol, pirbuterol, soterenol, terbutaline, tulobuterol and their possible stereoisomeric forms or biological precursors.

6. A transdermal therapeutic system according to claim 1 in which the active ingredient is broxaterol in amount from 20% to 40% by weight.

7. A transdermal therapeutic system according to claim 1 in which the active ingredient is albuterol in amount from 20% to 40% by weight.

* * * * *